United States Patent
Gao et al.

(10) Patent No.: US 7,684,933 B2
(45) Date of Patent: Mar. 23, 2010

(54) AUTOMATED INTELLIGENT SYSTEM FOR LUBRICANT MANUFACTURE OPTIMIZATION

(75) Inventors: Jason Z. Gao, Rose Valley, NJ (US); Peter Calcavecchio, Milford, NJ (US); Medi M. Hafez, Sarnia (CA); Joan M. Kaminski, Wallingford, PA (US); Liehpao Oscar Farng, Lawrenceville, NJ (US); David A. Blain, Cherry Hill, NJ (US); Gene Sanchez, Pitman, NJ (US); Janet L. Lane, Haddonfield, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 11/982,893

(22) Filed: Nov. 6, 2007

(65) Prior Publication Data

US 2008/0140366 A1      Jun. 12, 2008

Related U.S. Application Data

(60) Provisional application No. 60/860,427, filed on Nov. 21, 2006.

(51) Int. Cl.
    *G01N 31/00*    (2006.01)
(52) U.S. Cl. ............................................ 702/25; 702/27
(58) Field of Classification Search .................. 702/22, 702/23, 25, 27, 30; 703/2, 6, 10, 12; 705/400; 508/110; 73/53.01, 53.05
See application file for complete search history.

(56) References Cited

U.S. PATENT DOCUMENTS

| | | | | |
|---|---|---|---|---|
| 5,877,409 | A | * | 3/1999 | Girling ..................... 73/54.06 |
| 6,295,485 | B1 | * | 9/2001 | Gleeson et al. ............. 700/272 |
| 7,392,142 | B2 | * | 6/2008 | Kaldor et al. ................. 702/22 |
| 7,449,432 | B2 | * | 11/2008 | Lockwood et al. .......... 508/113 |
| 7,494,961 | B2 | * | 2/2009 | Small et al. ................. 508/542 |
| 7,547,666 | B2 | * | 6/2009 | Loh et al. ................... 508/192 |
| 2006/0169031 | A1 | * | 8/2006 | Song et al. ................. 73/53.05 |
| 2007/0112527 | A1 | * | 5/2007 | McKay ....................... 702/22 |
| 2009/0037159 | A1 | * | 2/2009 | Wen et al. ...................... 703/6 |

FOREIGN PATENT DOCUMENTS

DE      197 12 614      * 10/1998
WO      2006/062885     * 6/2006

OTHER PUBLICATIONS

Michael Fowler, "Viscosity", UVa, Jun. 26, 2007.*
English Abstract of DE 197 12 614, Oct. 1998.*

* cited by examiner

*Primary Examiner*—Michael P Nghiem

(57) ABSTRACT

A method and system to blend components to form a lubricant having a predetermined characteristic. The method includes determining the characteristic from a model that relates that characteristic as a function of the amount of its components and properties of the components. These predetermined characteristics include KV (kinematic viscosities), CCS (cold cranking simulator), HTHS (high temperature, high shear viscosity), Noack Volatility, MRV (mini-rotary viscometer), Brookfield Viscosity, Soot-Dispersancy, Oxidation, Deposit, Wear, Sulfur, Phosphorus, Base Number, Color, Ash Content, Aniline Point, Acid Number, Viscosity Index, Turbidity, Demulsibility, Foam Stability, Acute Toxicity, Biodegradability, Nitrogen, and Detergency.

10 Claims, 5 Drawing Sheets

FIG. 1 - TGA Weight vs. Time

AUTOMATED INTELLIGENT SYSTEM FOR LUBRICANT MANUFACTURE OPTIMIZATION

CROSS-REFERENCE TO RELATED APPLICATION

This application claims the benefit of U.S. Provisional application 60/860,427 filed Nov. 21, 2006.

BACKGROUND OF THE INVENTION

The present invention relates to a system and method for lubricant manufacture. In particular, the invention relates to the blending of raw materials to form a lubricant having predetermined characteristics.

In the prior art, lubricant blending is based on fixed formulations generated from laboratories. The raw materials used are usually derived from petroleum processes and there are significant batch-to-batch variations. Therefore, the finished oil properties such as viscosity and metal contents usually reflect the variations in raw materials. The variations in raw materials as well as in finished lubricants are the limiting factors for continuous improvement in blending capability. In recent years, new specifications such as volatility and sulfur content had been added to automotive engine lubricants, making it even harder to blend lubricants meeting multiple specifications Recent advances in in-line or batch blending technology allow high level of automation in lubricant blending. However, little progress has been made in addressing the issues related to raw material variations and finished lubricant optimization.

The present invention includes a system and method for lubricant manufacture, in which the finished lubricants manufactured using this system and method are a combination of raw materials that result in a lubricant having predetermined characteristics. Furthermore, these lubricants show significant reduction in variations in viscosity and other parameters.

SUMMARY OF THE INVENTION

The present invention is a system and a method to blend components to form lubricants having predetermined characteristics. This is done by using models that relate lubricant characteristics to a combination of the amounts of raw materials (components) and characteristics (properties) of the raw materials.

DETAILED DESCRIPTION OF THE PREFERRED EMBODIMENTS

Figure 1:
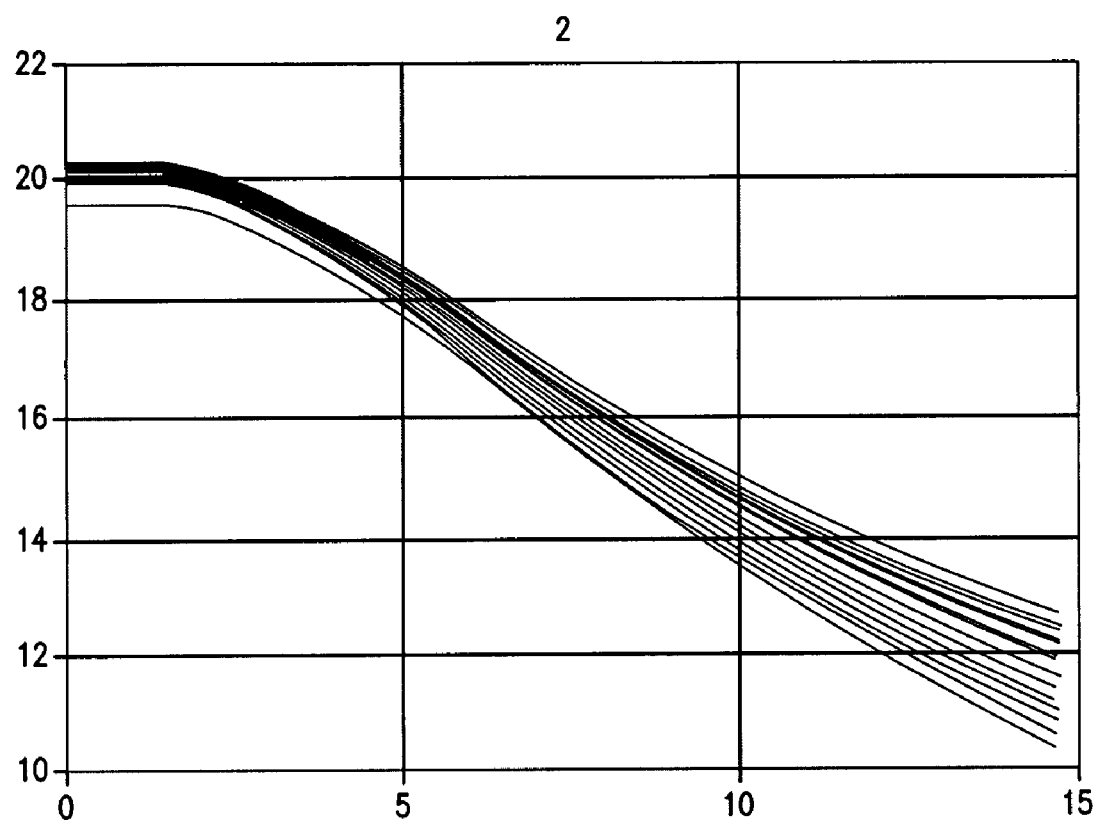
FIG. 1 shows a graph of weight (loss of retention) vs. time for a sample according to the present invention.

Modern lubricants contain multiple basestocks and additives and are manufactured to meet multiple specifications such as kinematic viscosity, cold cranking simulator viscosity, and volatility. Traditional approach of blending lubricants with fixed formulations cannot account for the variation in raw materials. In order to produce optimal products, the formulations need to be adjusted based on blends at the laboratory or by using mathematical models. The present invention includes a system and method including lab-scale high throughput blending and testing, mathematical modeling, on-line sensors, and lubricant manufacture automation.

Most of lubricant blend plants essentially use fixed formulations today. In some cases, the basestock ratio is adjusted to meet a base oil (or mineral oil) viscosity target (MOV). Some lubricant blend plants have been using more sophisticated models to guide lubricant blending by adjusting basestock and viscosity modifier treat levels to meet viscosity targets. The present invention is an innovative and novel extension of this approach by combining mathematical modeling with high-throughput lab-scale blending and production automation.

Lubricant Additives

Lubricant additives or components include, but are not limited to, viscosity modifiers, dispersants, detergents, pour point depressants, oil thickeners, polyisobutylenes, high molecular weight polyalphaolefins, antiwear/extreme pressure agents, antioxidants, demulsifiers, seal swelling agents, friction modifiers, corrosion inhibitors, and antifoam additives, as well as performance packages containing mixtures of these lubricant additives, such as for example mixtures of dispersants, detergents, antiwear/extreme pressure agents, antioxidants, demulsifiers, seal swelling agents, friction modifiers, corrosion inhibitors, antifoam additives, and pour point depressants. High viscosity lubricants include, but are not limited to, viscosity modifiers, pour point depressants, dispersants, polyisobutylenes, and high molecular weight polyalphaolefins and additive packages containing one or more of these high viscosity lubricants. The disclosed method of blending lubricant additives using positive-displacement liquid-handling equipment method also allows blending to be done with minimal chemical, thermal or physical degradation of the high viscosity lubricant components within the lubricant blend.

Viscosity Modifiers

Viscosity modifiers (also known as VI improvers and viscosity index improvers) provide lubricants with high and low temperature operability. These additives impart shear stability at elevated temperatures, and acceptable viscosity at low temperatures.

Suitable viscosity index improvers include high molecular weight (polymeric) hydrocarbons, polyesters and viscosity index improver dispersants that function as both a viscosity index improver and a dispersant. Typical molecular weights of these polymers are between about 10,000 to 1,000,000, more typically about 20,000 to 500,000, and even more typically between about 50,000 and 200,000.

Examples of suitable viscosity index improvers are polymers and copolymers of methacrylate, butadiene, olefins, or alkylated styrenes. Polyisobutylene is a commonly used viscosity index improver. Another suitable viscosity index improver is polymethacrylate (copolymers of various chain length alkyl methacrylates, for example), some formulations of which also serve as pour point depressants. Other suitable viscosity index improvers include copolymers of ethylene and propylene, hydrogenated block copolymers of styrene and isoprene, and polyacrylates (copolymers of various chain length acrylates, for example). Specific examples include olefin copolymer and styrene-hydrogenated isoprene copolymer of 50,000 to 200,000 molecular weight.

Viscosity modifiers are used in an amount of about 1 to 25 wt % on an as received basis. Because viscosity modifiers are usually supplied diluted in a carrier or diluent oil and constitute about 5 to 50 wt % active ingredient in the additive concentrates as received from the manufacturer, the amount of viscosity modifiers used in the formulation can also be expressed as being in the range of about 0.20 to about 3.0 wt % active ingredient, preferably about 0.3 to 2.5 wt % active ingredient. For olefin copolymer and styrene-hydrogenated isoprene copolymer viscosity modifier, the active ingredient is in the range of about 5 to 15 wt % in the additive concentrates from the manufacturer, the amount of the viscosity modifiers used in the formulation can also be expressed as being in the range of about 0.20 to 1.9 wt % active ingredient, and preferably about 0.3 to 1.5 wt % active ingredient.

Dispersants

During engine operation, oil-insoluble oxidation byproducts are produced. Dispersants help keep these byproducts in solution, thus diminishing their deposition on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

Chemically, many dispersants may be characterized as phenates, sulfonates, sulfurized phenates, salicylates, naphthenates, stearates, carbamates, thiocarbamates, phosphorus derivatives. A particularly useful class of dispersants are the alkenylsuccinic derivatives, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Many examples of this type of dispersant are well known commercially and in the literature. Exemplary U.S. patents Nos. describing such dispersants, and incorporated by reference in their entirety, are U.S. Pat. Nos. 3,172,892; 3,2145,707; 3,219,666; 3,316,177; 3,341,542; 3,444,170; 3,454,607; 3,541,012; 3,630,904; 3,632,511; 3,787,374 and 4,234,435. Other types of dispersant are described in U.S. Pat. Nos. 3,036,003; 3,200,107; 3,254,025; 3,275,554; 3,438,757; 3,454,555; 3,565,804; 3,413,347; 3,697,574; 3,725,277; 3,725,480; 3,726,882; 4,454,059; 3,329,658; 3,449,250; 3,519,565; 3,666,730; 3,687,849; 3,702,300; 4,100,082; 5,705,458, also incorporated by reference in their entirety. A further description of dispersants may be found, for example, in European Patent Application No. 471 071, also incorporated by reference in its entirety.

Hydrocarbyl-substituted succinic acid compounds are popular dispersants. In particular, succinimide, succinate esters, succinic acid amine salts, succinic acid derived imidazoles or oxazolines, or succinate ester amides prepared by the reaction of a hydrocarbon-substituted succinic acid compound preferably having at least 50 carbon atoms in the hydrocarbon substituent, with at least one equivalent of an alkylene amine or hydroxyl alkylene amine are particularly useful.

Succinimides are formed by the condensation reaction between alkenyl succinic anhydrides and amines. Molar ratios can vary depending on the polyamine. For example, the molar ratio of alkenyl succinic anhydride to TEPA can vary from about 1:1 to about 5:1. Representative examples are shown in U.S. Pat. Nos. 3,087,936; 3,172,892; 3,219,666; 3,272,746; 3,322,670; and 3,652,616, 3,948,800; and Canada Pat. No. 1,094,044, all of which are incorporated by reference in their entirety.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenyl-polyamines such as polyethylene polyamines. One example is propoxylated hexamethylenediamine. Representative examples are shown in U.S. Pat. No. 4,426,305, which is incorporated by reference in its entirety.

The molecular weight of the alkenyl succinic anhydrides used in the preceding paragraphs will typically range between 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from about 0.1 to about 5 moles of boron per mole of dispersant reaction product.

Mannich base dispersants are made from the reaction of alkylphenols, formaldehyde, and amines. See U.S. Pat. No. 4,767,551, which is incorporated herein by reference. Process aids and catalysts, such as oleic acid and sulfonic acids, can also be part of the reaction mixture. Molecular weights of the alkylphenols range from 800 to 2,500. Representative examples are also shown in U.S. Pat. Nos. 3,697,574; 3,703, 536; 3,704,308; 3,751,365; 3,756,953; 3,798,165; and 3,803, 039, all of which are herein incorporated by reference in their entirety.

Typical high molecular weight aliphatic acid modified Mannich condensation products useful in this invention can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include the mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamide reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N-(Z-NH-)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloroalkanes having 2 to 6 carbon atoms and the chlorines on different carbons are suitable alkylene polyamine reactants.

Aldehyde reactants useful in the preparation of the high molecular products useful in this invention include the aliphatic aldehydes such as formaldehyde (also as paraformaldehyde and formalin), acetaldehyde and aldol (β-hydroxybutyraldehyde). Formaldehyde or a formaldehyde-yielding reactant is preferred.

Hydrocarbyl substituted amine ashless dispersant additives are disclosed, for example, in U.S. Pat. Nos. 3,275,554; 3,438,757; 3,565,804; 3,755,433; 3,822,209 and 5,084,19; all of which are herein incorporated by reference.

Preferred dispersants include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000 or a mixture of such hydrocarbylene groups. Other preferred dispersants include succinic acid-esters and amides, alkylphenol-polyamine-coupled Mannich adducts, their capped derivatives, and other related components. Such additives may be used in an amount of about 0.1 to 20 wt %, preferably about 0.1 to 8 wt %.

Pour Point Depressants

Conventional pour point depressants (also known as lube oil flow improvers) may be added to the compositions of the present invention if desired. These pour point depressant may be added to lubricating compositions of the present invention to lower the minimum temperature at which the fluid will flow or can be poured. Examples of suitable pour point depressants include polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. U.S. Pat. Nos. 1,815,022; 2,015,748; 2,191,498; 2,387,501; 2,655,479; 2,666,746; 2,721,877; 2,721,878; and 3,250,715, all of which are herein incorporated by reference, describe useful pour point depressants and/or the preparation thereof. Such additives may be used in an amount of about 0.01 to 5 wt %, preferably about 0.01 to 1.5 wt %.

Typical Additive Amounts

When lubricating oil compositions contain one or more of the additives discussed above, the additive(s) are blended into the composition in an amount sufficient for it to perform its intended function. Exemplary amounts of such additives useful in the present invention are depicted in Table 1 below. Note that many of the additives are shipped from the manufacturer and used with a certain amount of base oil solvent in the formulation. Accordingly, the weight amounts in the table below, as well as other amounts referenced in the present disclosure, unless otherwise indicated, are directed to the amount of active ingredient (that is the non-solvent portion of the ingredient). The weight percentages indicated below are based on the total weight of the lubricating oil composition.

TABLE 1

Typical Amounts of Various Lubricant Oil Components

| Compound | Approximate Wt % (Useful) | Approximate Wt % (Preferred) |
| --- | --- | --- |
| Viscosity Modifier | 1-25 | 3-20 |
| Detergent | 0.01-6 | 0.01-4 |
| Dispersant | 0.1-20 | 0.1-8 |
| Friction Reducer | 0.01-5 | 0.01-1.5 |
| Antioxidant | 0.0-5 | 0.0-1.5 |
| Corrosion Inhibitor | 0.01-5 | 0.01-1.5 |
| Anti-wear Additive | 0.01-6 | 0.01-4 |
| Pour Point Depressant | 0.0-5 | 0.01-1.5 |
| Anti-foam Agent | 0.001-3 | 0.001-0.15 |
| Base Oil | Balance | Balance |

Groups I, II, III, IV and V are broad categories of base oil stocks developed and defined by the American Petroleum Institute (API Publication 1509; www.API.org) to create guidelines for lubricant base oils. Group I base stocks generally have a viscosity index of between about 80 to 120 and contain greater than about 0.03% sulfur and/or less than about 90% saturates. Group II base stocks generally have a viscosity index of between about 80 to 120, and contain less than or equal to about 0.03% sulfur and greater than or equal to about 90% saturates. Group III stock generally has a viscosity index greater than about 120 and contains less than or equal to about 0.03% sulfur and greater than about 90% saturates. Group IV includes polyalphaolefins (PAO). Group V base stocks include base stocks not included in Groups I-IV. Table 2 summarizes properties of each of these five groups.

TABLE 2

Base Stock Properties

| | Saturates | Sulfur | Viscosity Index |
| --- | --- | --- | --- |
| Group I | <90% and/or | >0.03% and | 80 and <120 |
| Group II | 90% and | 0.03% and | 80 and <120 |
| Group III | 90% and | 0.03% and | 120 |
| Group IV | Polyalphaolefins (PAO) | | |
| Group V | All other base oil stocks not included in Groups I, II, III, or IV | | |

Base stocks having a high paraffinic/naphthenic and saturation nature of greater than 90 weight percent can often be used advantageously in certain embodiments. Such base stocks include Group II and/or Group III hydroprocessed or hydrocracked base stocks, or their synthetic counterparts such as polyalphaolefin oils, GTL or similar base oils or mixtures of similar base oils.

GTL materials are materials that are derived via one or more synthesis, combination, transformation, rearrangement, and/or degradation/deconstructive processes from gaseous carbon-containing compounds, hydrogen-containing compounds, and/or elements as feedstocks such as hydrogen, carbon dioxide, carbon monoxide, water, methane, ethane, ethylene, acetylene, propane, propylene, propyne, butane, butylenes, and butynes. GTL base stocks and base oils are GTL materials of lubricating viscosity that are generally derived from hydro-carbons, for example waxy synthesized hydrocarbons, that are themselves derived from simpler gaseous carbon-containing compounds, hydrogen-containing compounds and/or elements as feedstocks. GTL base stock(s) include oils boiling in the lube oil boiling range separated/fractionated from GTL materials such as by, for example, distillation or thermal diffusion, and subsequently subjected to well-known catalytic or solvent dewaxing processes to produce lube oils of reduced/low pour point; wax isomerates, comprising, for example, hydroisomerized or isodewaxed synthesized hydrocarbons; hydro-isomerized or isodewaxed Fischer-Tropsch ("F-T") material (i.e., hydrocarbons, waxy hydrocarbons, waxes and possible analogous oxygenates); preferably hydroisomerized or isodewaxed F-T hydrocarbons or hydroisomerized or isodewaxed F-T waxes, hydroisomerized or isodewaxed synthesized waxes, or mixtures thereof.

GTL base stock(s) derived from GTL materials, especially, hydroisomerized/isodewaxed F-T material derived base stock(s), and other hydroisomerized/isodewaxed wax derived base stock(s) are characterized typically as having kinematic viscosities at 100° C. of from about 2 mm2/s to about 50 mm2/s, preferably from about 3 mm2/s to about 50 mm2/s, more preferably from about 3.5 mm2/s to about 30 mm2/s, as exemplified by a GTL base stock derived by the isodewaxing of F-T wax, which has a kinematic viscosity of about 4 mm2/s at 100° C. and a viscosity index of about 130 or greater. The term GTL base oil/base stock and/or wax isomerate base oil/base stock as used herein and in the claims is to be understood as embracing individual fractions of GTL base stock/base oil or wax isomerate base stock/base oil as recovered in the production process, mixtures of two or more GTL base stocks/base oil fractions and/or wax isomerate base stocks/base oil fractions, as well as mixtures of one or two or more low viscosity GTL base stock(s)/base oil fraction(s) and/or wax isomerate base stock(s)/base oil fraction(s) with one, two or more high viscosity GTL base stock(s)/base oil fraction(s) and/or wax isomerate base stock(s)/base oil fraction(s) to produce a dumbbell blend wherein the blend exhibits a viscosity within the aforesaid recited range. Reference herein to Kinematic viscosity refers to a measurement made by ASTM method D445.

GTL base stocks and base oils derived from GTL materials, especially hydroisomerized/isodewaxed F-T material derived base stock(s), and other hydroisomerized/isodewaxed wax-derived base stock(s), such as wax hydroisomerates/isodewaxates, which can be used as base stock components of this invention are further characterized typically as having pour points of about −5° C. or lower, preferably about −10° C. or lower, more preferably about −15° C. or lower, still more preferably about −20° C. or lower, and under some conditions may have advantageous pour points of about −25° C. or lower, with useful pour points of about −30° C. to about −40° C. or lower. If necessary, a separate dewaxing step may be practiced to achieve the desired pour point. References herein to pour point refer to measurement made by ASTM D97 and similar automated versions.

The GTL base stock(s) derived from GTL materials, especially hydroisomerized/isodewaxed F-T material derived base stock(s), and other hydroisomerized/isodewaxed wax-derived base stock(s) which are base stock components which can be used in this invention are also characterized typically as having viscosity indices of 80 or greater, preferably 100 or greater, and more preferably 120 or greater. Additionally, in certain particular instances, viscosity index of these base stocks may be preferably 130 or greater, more preferably 135 or greater, and even more preferably 140 or greater. For example, GTL base stock(s) that derive from GTL materials preferably F-T materials especially F-T wax generally have a viscosity index of 130 or greater. References herein to viscosity index refer to ASTM method D2270.

In addition, the GTL base stock(s) are typically highly paraffinic of greater than 90 percent saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stocks and base oils typically have very low sulfur and nitrogen content, generally containing less than about 10 ppm, and more typically less than about 5 ppm of each of these elements. The sulfur and nitrogen content of GTL base stock and base oil obtained by the hydroisomerization/isodewaxing of F-T material, especially F-T wax is essentially nil.

Useful compositions of GTL base stock(s), hydroisomerized or isodewaxed F-T material derived base stock(s), and wax-derived hydroisomerized/isodewaxed base stock(s), such as wax isomerates/isodewaxates, are recited in U.S. Pat. Nos. 6,080,301; 6,090,989, and 6,165,949 for example.

Commercial additive packages usually include, but are not limited to, one or more detergents, dispersants, friction reducers, antioxidants, corrosion inhibitors, and anti-wear additives.

On-line sensors are used in selected blend plants, but adjustments of the component treats are made manually since there are no mathematical models to guide the adjustment and correction.

The present invention includes a system and method that can automatically blend the optimal formulation of a lubricant to meet multiple specifications. The following determinations are involved both in system and process:

1. Generating mathematical models by use of lab-scale high-throughput experimentation techniques.
2. Determining the optimal blend formulation based on the models as well as the raw material properties and costs.
3. Adjusting the blend during or after blending based on the models and the measurements on the blended product.

On-line sensors can be used in the raw material and the blended product tanks to send data back to the computer system.

The lab-scale high throughput blending and testing of lubricants could be conducted in a separate laboratory or at the manufacturing site, using the side streams from the production lines. The lab-scale high throughput blender could be a commercial liquid handling device like those marketed by Tecan, Zinsser, or Symyx, or a custom-made device with a mini-inline mixer.

Although most commercial liquid handling devices are designed for aqueous systems (typically used in biotechnology applications such as pharmaceutical and medical), the following modifications were made to adapt a Tecan model RSP 100 robot to lubricant handling:

1. Change the system fluid from water (typically used and recommended by the manufacturer) to a hydrocarbon. Ideally the system fluid should be compatible with the principle components in the lubricant being blended, to minimize changes in lubricant properties if cross contaminated with system fluid. A lubricant base stock was chosen to be the system fluid, with its viscosity matched to be high enough to provide plug flow in the tips (to minimize cross contamination) and low enough to avoid stalling the syringe pumps on the Tecan.

2. The tapered part of the "wide bore" tips purchased from Tecan were cut (on a diagonal) to increase the diameter from 0.8 mm to 1.5 mm. This change was made to improve the flow of higher viscosity lubricant components in and out of the tips. The diagonal cut is polished to provide a sharp edge to pierce septa capped vials and bottles.

3. The aspirating and dispense speeds and delays were optimized to handle as wide a range of viscosity and sample size as possible. These included:
   a. Slow aspirating speed followed by a delay
   b. Fast dispense speeds
   c. An air gap to separate component and system fluid
   d. An air plug to dispense very small volumes 4. Heated blocks were added to lower the viscosity of lubricant components in source containers. Also optional tips were made with heating elements to maintain lower viscosity while transferring the components from the source to the destination containers.

5. A pump was added to provide fast dispense of lower viscosity and high volume components. Also the pump provides for fast rinsing of the tips after dispensing components.

In some cases, balances are added to measure the addition of the each component by weight. The addition of each component is adjusted by the computer based on the amount already added and measured by the balance. In addition, positive-displacement pipettes from Gibson and Eppendorf can also be incorporated in some liquid handling devices such as the Zinsser WinLissy system.

The lubricant formulations dispensed using the liquid handling devices is mixed in a Certomat BS-1 heated incubator from Sartorius for about 2 to 5 hours at about 200-500 rmp, and at a temperature between 50 and 80 C.

A series of measurements are then conducted on the blended lubricants including kinematic viscosities (KV), cold cranking simulator (CCS) viscosities, volatilities, and other physico-chemical properties. A Houillon viscometer with automated sampling system from Caliper Life Science is used for kinematic viscosity measurements and a commercial Cannon Cold Cranking Simulator (CCS) is used for CCS measurements.

TGA (thermal gravimetric analysis) is known to correlate to Noack volatility measurements as described in ASTM method D6375. Using this method, one calculates the Noack value by determining the evaporative weight loss in the TGA at a specified time determined by running a reference oil. In the present invention, a different approach was used to generate TGA data to correlate with Noack volatility as described in the procedure below.

Equipment

The test equipment is a Model Q-500 available from TA Instruments, although other TGA units (for example, TA's Model Q-5000, Netzsch 209C and 209F1) may be used if an autosampler is available. The gas flow rates are regulated inside the equipment to ensure sufficient amounts of carrier gases are used to protect the furnace and micro-balance from being contaminated, as well as maintaining constant flow rates for the proper control of evaporation rate, respectively.

Calibration

The normal calibration procedure as recommended by the manufacturer is utilized. In addition to temperature calibration to ensure the proper furnace temperature control, internal standards can be established to verify run-to-run repeatability and reproducibility. At least one sample per every 16 samples is used as an internal standard. The repeatability of the internal standard is monitored and recorded periodically.

Procedure

In order to avoid temperature overshoot, multi-stage ramping is used in combination with an isothermal period as described in the example below:

a. Stage 1: ramp@100° C./minute from ambient temperature to 220° C.
b. Stage 2: ramp@10° C./minute from 220° C. to 249° C.
c. Stage 3: maintain an isothermal mode for 10 minutes
d. Stage 4: cool down to temperature <40° C.

Other temperature ramping profiles can also be utilized.

Autosampler

An autosampler is used to generate data in a high throughput experimentation mode. The general procedure requires (a) tare the 16 empty pans in sequence, (b) inject and weigh 16 samples into each sample pans, and (c) run 16 samples in sequence.

Sample

Sample size can range from 10 mg to 50 mg if 100 µL sample pan is used. For comparison purpose, it is important to maintain as close to a constant sample size as possible and also keep the air flow rates constant.

Sample can be injected into sample pans through pipettes. Automated dispensing system may also be used to accelerate dispensing rate. However, the special geometry of sample pans (with V-shape hook on top) make designing the automation system difficult.

There are a number of sample pans available. Platinum or aluminum pans can be used due to their inertness and ease of cleaning.

Data Analysis

Data can be plotted by measuring weight (loss or retention) of sample versus temperature or time. This is illustrated in FIG. 1.

Since multi-stage heating and isotherm are involved, a plot of % weight loss (by every 5 wt % increment) or % weight retention (by every 5 wt % decrement) versus time can also be graphed. In other words, the generation of a set of data based on 5 or more (X,Y) is sufficient, where X is the % weight retention to the original weight (i.e. 95%, 90%, 85%, 80%, 75% . . . ) and Y is the time in minutes.

Figure 2:
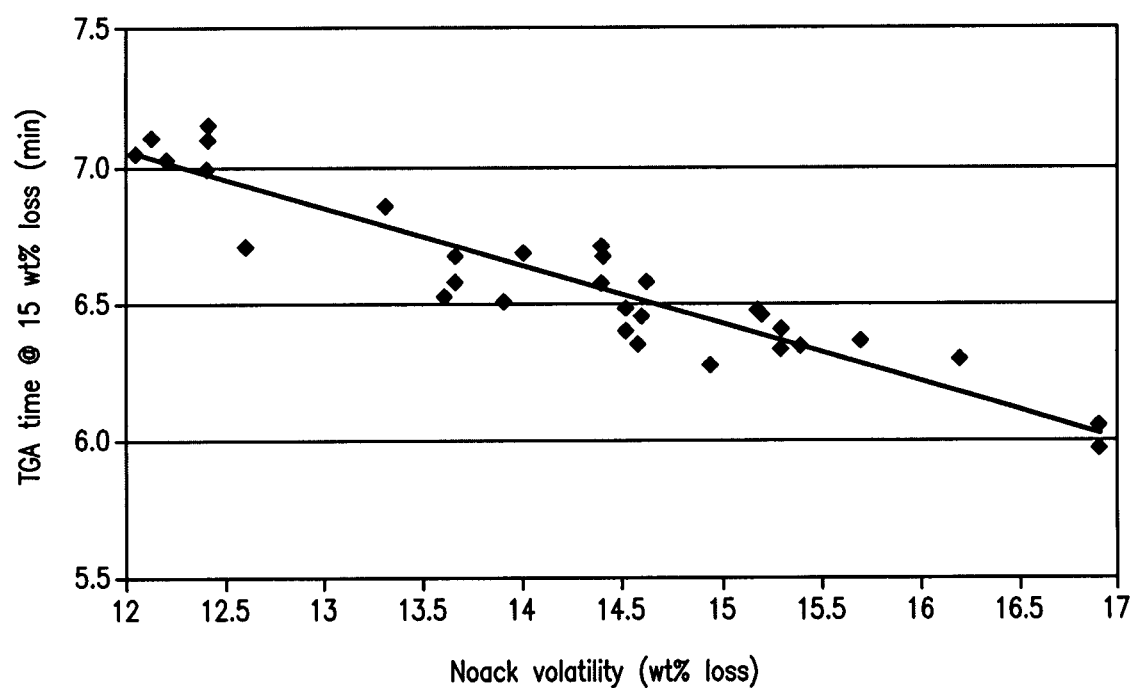
FIG. 2 shows correlations based on a group of oils of similar formation chemistry.

Once the % weight versus time plots are available, possible correlations can be established by analyzing the sample data set against the actual Noack measurements (ASTM D5800-B method). Simple linear equations can be derived based on a group of oils of similar formulation chemistry. This is illustrated in FIG. 2.

Clean-Up

Frequent cleaning is needed to keep the system clean and to avoid condensation/contamination carried from sample to sample. A visual inspection of the hang-down wire and surrounding area is an effective way to determine whether a clean-up is needed. The general clean-up procedure includes a quick ramping to 700 or 750° C. and maintaining at that temperature for 30-45 minutes to burn-off all residues.

Figure 3:
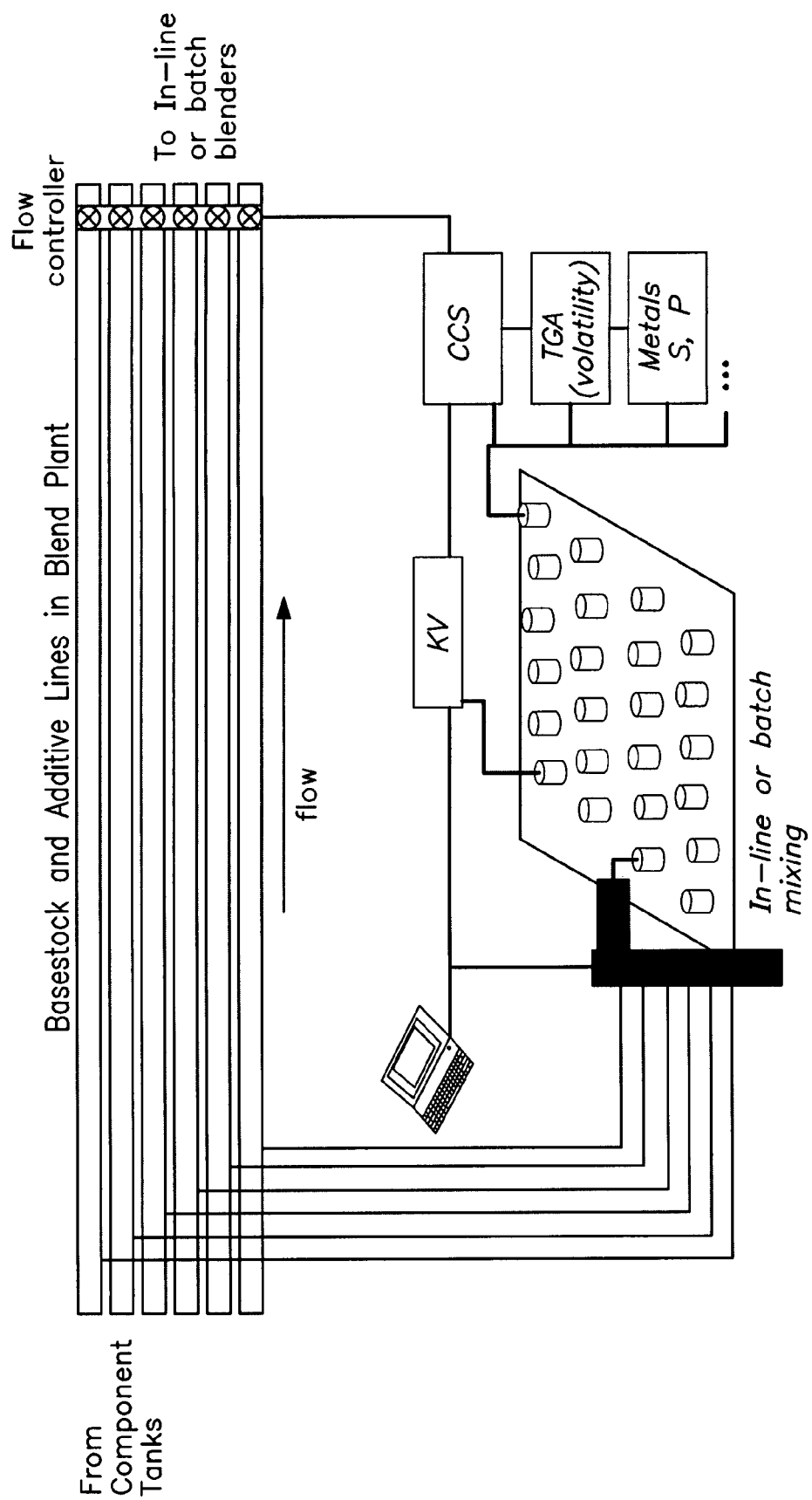
FIG. 3 shows a schematic drawing of one embodiment of the system of the present invention.

FIG. 3 shows a high throughput blending and testing station in a lubricant blend plant.

The other high throughput tests used may also include but are not limited to FTIR, and Tapered Bearing Simulator (for high temperature, high shear viscosity or HTHS), mini-rotary viscometer (MRV), Brookfield viscometer, and base and acid numbers, and elemental analysis. High throughput lubricant performance tests such as oxidation, deposit, wear, corrosion, detergency, and storage stability tests might also be added.

The viscometric, compositional, and other performance parameters for a finished lubricant blend can be described as a function of its composition and some of the properties of its components:

$$KV = f_1(X_1, X_2, X_3 \ldots, P_1, P_2, P_3 \ldots) \quad (1)$$

$$CCS = f_2(X_1, X_2, X_3 \ldots, P_1, P_2, P_3 \ldots) \quad (2)$$

$$HTHS = f_3(X_1, X_2, X_3 \ldots, P_1, P_2, P_3 \ldots) \quad (3)$$

$$\text{Noack Volatility} = f_4(X_1, X_2, X_3 \ldots, P_1, P_2, P_3 \ldots) \quad (4)$$

$$MRV = f_5(X_1, X_2, X_3 \ldots, P_1, P_2, P_3 \ldots) \quad (5)$$

$$\text{Brookfield Viscosity} = f_6(X_1, X_2, X_3 \ldots, P_1, P_2, P_3 \ldots) \quad (6)$$

$$\text{Soot-dispersancy} = f_7(X_1, X_2, X_3 \ldots, P_1, P_2, P_3 \ldots) \quad (7)$$

$$\text{Oxidation} = f_8(X_1, X_2, X_3 \ldots, P_1, P_2, P_3 \ldots) \quad (8)$$

$$\text{Deposit} = f_9(X_1, X_2, X_3 \ldots, P_1, P_2, P_3 \ldots) \quad (9)$$

$$\text{Wear} = f_{10}(X_1, X_2, X_3 \ldots, P_1, P_2, P_3 \ldots) \quad (10)$$

$$\text{Sulfur} = f_{11}(X_1, X_2, X_3 \ldots, P_1, P_2, P_3 \ldots) \quad (11)$$

$$\text{Phosphorus} = f_{12}(X_1, X_2, X_3 \ldots, P_1, P_2, P_3 \ldots) \quad (12)$$

$$\text{Base Number (BN)} = f_{13}(X_1, X_2, X_3 \ldots, P_1, P_2, P_3 \ldots) \quad (13)$$

$$\text{Color} = f_{14}(X_1, X_2, X_3 \ldots, P_1, P_2, P_3 \ldots) \quad (14)$$

$$\text{Ash Content} = f_{15}(X_1, X_2, X_3 \ldots, P_1, P_2, P_3 \ldots) \quad (15)$$

$$\text{Aniline Point} = f_{16}(X_1, X_2, X_3 \ldots, P_1, P_2, P_3 \ldots) \quad (16)$$

$$\text{Acid Number (AN)} = f_{17}(X_1, X_2, X_3 \ldots, P_1, P_2, P_3 \ldots) \quad (17)$$

$$\text{Viscosity Index} = f_{18}(X_1, X_2, X_3 \ldots, P_1, P_2, P_3 \ldots) \quad (18)$$

$$\text{Turbidity} = f_{19}(X_1, X_2, X_3 \ldots, P_1, P_2, P_3 \ldots) \quad (19)$$

$$\text{Demulsibility} = f_{20}(X_1, X_2, X_3 \ldots, P_1, P_2, P_3 \ldots) \quad (20)$$

$$\text{Foam Stability} = f_{21}(X_1, X_2, X_3 \ldots, P_1, P_2, P_3 \ldots) \quad (21)$$

$$\text{Acute Toxicity} = f_{22}(X_1, X_2, X_3 \ldots, P_1, P_2, P_3 \ldots) \quad (22)$$

$$\text{Biodegradability} = f_{23}(X_1, X_2, X_3 \ldots, P_1, P_2, P_3 \ldots) \quad (23)$$

$$\text{Nitrogen} = f_{24}(X_1, X_2, X_3 \ldots, P_1, P_2, P_3 \ldots) \quad (24)$$

$$\text{Detergency} = f_{25}(X_1, X_2, X_3 \ldots, P_1, P_2, P_3 \ldots) \quad (25)$$

Where $X_1, X_2, X_3 \ldots$ are the wt %, vol %, or the mole fractions of components 1, 2, 3 . . . , and $P_1, P_2, P_3 \ldots$ are a subset of the properties of the corresponding components.

The functions for these properties may differ greatly and may or may not additionally contain these $P_i$ measurable properties such as viscosity, BN, and oxidation parameter of the raw material.

EXAMPLE 1

Rheological Properties

For rheological properties such as KV, CCS, and HTHS, the following equation could be used for a mixture of two components:

$$\ln \eta = X_1(\ln \eta_1 + A_1) + X_2(\ln \eta_2 + A_2) + A_0 \quad (26)$$

where $\eta$ is the rheological property of a mixture and $\eta_1$, and $\eta_2$ are the corresponding component rheological properties. $X_1, X_2$ are the weight fractions of component 1 and component 2 and $A_1, A_2$, and $A_0$ are constants. In general, $\eta_1$, and $\eta_2$ are measured properties. However, in some special cases, $\eta_1$, and $\eta_2$ are calculated from different properties based on correlations.

EXAMPLE 2

Formulation-Specific Modeling Approach

Figure 4:
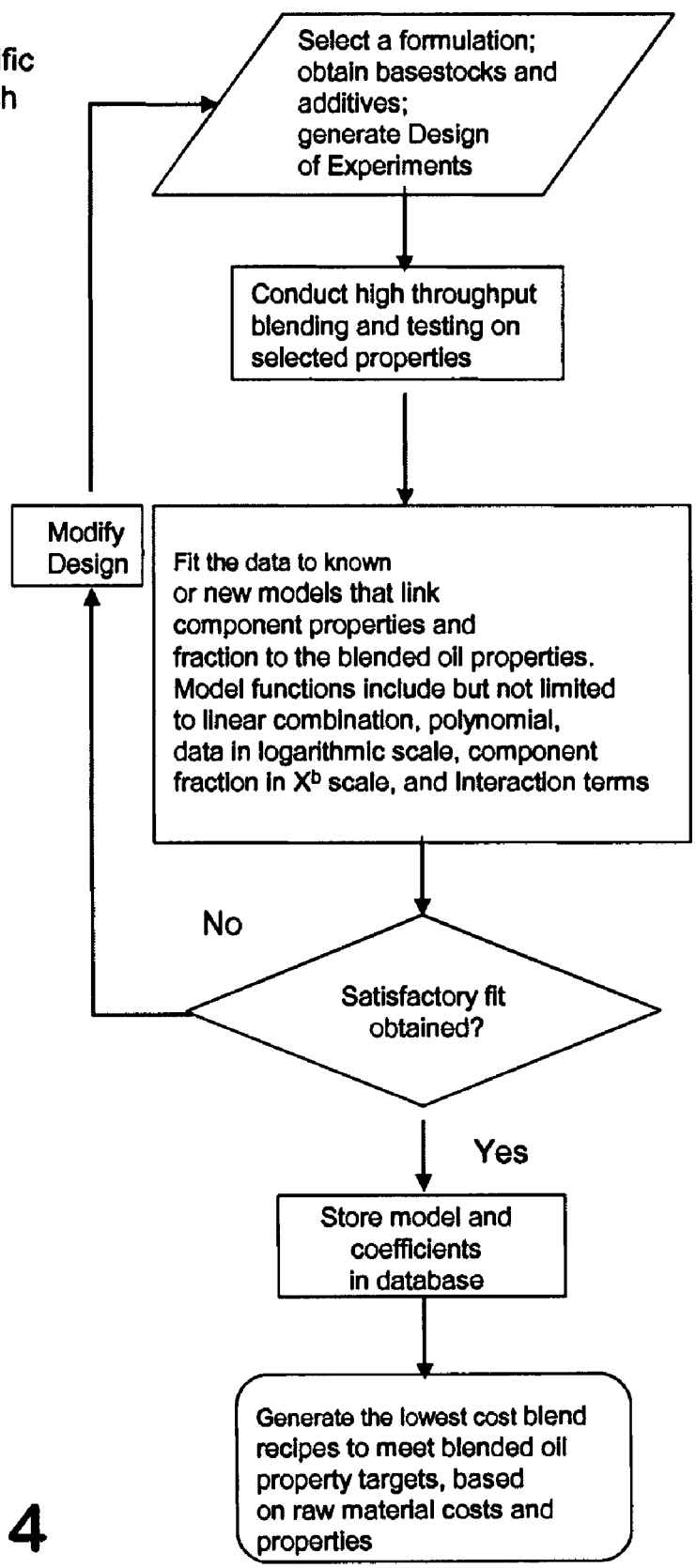
FIG. 4 shows a flow chart for a formulation-specific modeling approach.

FIG. 4 shows a flow-chart for a formulation-specific modeling approach when a formulation-specific modeling approach is used for rheological properties, the $A_1$ and $A_2$ and $A_0$ in Equation (26) are coefficients unique to the specific formulation

EXAMPLE 3

Component Modeling Approach

Figure 5:
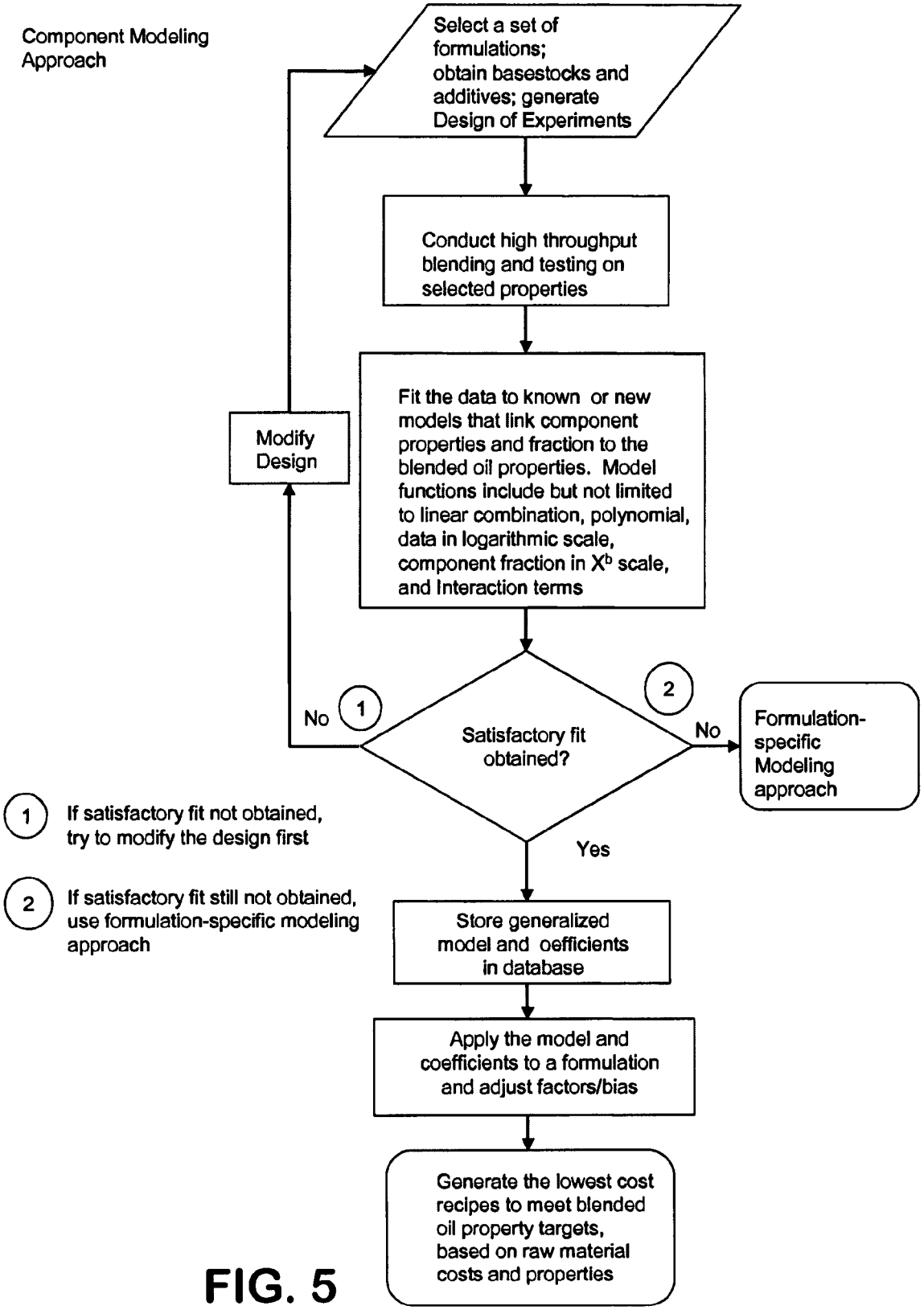
FIG. 5 shows a flow chart for a component modeling approach.

FIG. 5 shows a flow chart for a component modeling approach. When a component modeling approach is used for rheological properties, the $A_1$ and $A_2$ in Equation (26) are coefficients unique to Component 1 and Component 2 in all formulations. $A_0$ is constant unique to the formulation and can be obtained from historical data from laboratory or from commercial production.

EXAMPLE 4

Linear Properties

Properties related to the elements in a blend such as sulfur, nitrogen, boron, phosphorus, calcium, magnesium, as well as other properties such as Noack, base number and acid number, the following linear equation could be used for a mixture of two components.

$$T = X_1 T_1 + X_2 T_2 + T_0 \quad (27)$$

where T is a linear property of the mixture and $T_1$, and $T_2$ are the corresponding component properties. $X_1, X_2$ are the weight fractions of component 1 and component 2. $T_0$ is a constant unique to the formulation and can be obtained from a calibration blend from laboratory or from commercial production.

EXAMPLE 5

Multiple Component Formulations

When the mixtures contains more than two components, Equations (26) and (27) are expanded to:

$$\ln \eta = \Sigma X_i (\ln \eta_i + A_i) + A_0 \quad (28)$$

$$T = \Sigma X_i T_i + T_0 \quad (29)$$

Where i=1 to n

EXAMPLE 6

Non-Linear Blending Functions

The functions $f_i$ are not limited to linear functions. Any type of non-linear function is possible. For example:

$$\ln \eta = \Sigma_i X_i \ln \eta_i + \Sigma_{ij} X_i X_j g(\delta_i, \delta_j) + A_0 \quad (30)$$

Where i or j are all or a subset of 1 to n, $\delta_i$ and $\delta_j$ are solubility or other function, e.g., $g(\delta_i, \delta_j) = (\delta_i - \delta_j)^2$ The functions and the constants for a given formulation or a given family of formulations are determined by building a multivariate prediction model of the properties of interest, from the component concentrations and properties from a matrix of blends, using a sensible design of the experiments (DOE).

When the properties of the components ($P_1$, $P_2$, $P_3$) are known, these equations can then be solved simultaneously to obtain a composition (e.g., $X_1$=60 $X_2$=10, $X_3$=6.0 . . . ) meeting the specifications of KV, CCS, HTHS, Noack volatility, MRV, Brookfield viscosity, soot-dispersancy, oxidation, deposit, wear, sulfur, phosphorus, nitrogen, base number, acid number, detergency, as well as the other properties of interest. If multiple solutions are found, the lower cost option is usually chosen. In some special cases, optimized solutions may be based on the availability of a certain components.

When the optimized recipes are calculated, the computer can schedule the planned production blends and control the valves to add the right amount of components to the in-line blender or the blending vessels.

If the blend made is found outside of the specifications through quality assurance testing, the models are used to adjust the blend by calculating the additional quantities of certain components needed to bring the off-specification blend to the specification range.

On-line sensors can be installed in the component and finished lubricant tanks to send signals to the computer system. The signals from the on-line sensors are processed and adjustments to the lubricants are made if necessary using the mathematical models or the on-line sensors.

The connection between the computer and the various devices could also be wireless.

A natural extension of this invention would require no a priory knowledge of the properties of the individual batches of components, but would utilize an establish database of typical values for each of the components. The adjustment factors for the blend would then be modeled in real time, with the blend component ratios adjusted dynamically with the integrated target of meeting the specifications on the finished tank. With proper flow metering of key components, and the total blend, these dynamic variations on key components would provide sufficient variance to model the deviations from the typical properties of those components.

For example, in equation (26) above, we could use typical values for $\eta_1$ $\eta_2$ and $A_0$, and estimate $A_1$ and $A_2$ dynamically. While the estimates of A1 and A2 would not be as accurate as a well designed experiment, the blend would dynamically converge to the target properties, within the accuracy of the high-throughput or in-line sensors. This uses the well known principle of combining multiple pieces of information low signal-to-noise information to obtain a high accuracy integrated result. The higher the throughput of the measurement technique, the higher the accuracy of the integrated blend result.

What is claimed is:

1. A method to blend components to form a finished lubricant having a predetermined characteristic from base stocks and additives comprising:

(a) blending the base stocks and additives is determined by a computer model that relates that a characteristic of a lubricant to the amount and properties and costs of its the base stocks and additives corresponding to the predetermined characteristic wherein said predetermined characteristic includes one or more of the predetermined characteristics $KV=f_1(X_1, X_2, X_3 \ldots, P_1, P_2, P_3 \ldots)$, $CCS=f_2(X_1, X_2, X_3 \ldots, P_1, P_2, P_3 \ldots)$, $HTHS=f_3(X_1, X_2, X_3 \ldots, P_1, P_2, P_3 \ldots)$, Noack Volatility=$f_4(X_1, X_2, X_3 \ldots, P_1, P_2, P_3 \ldots)$, $MRV=f_5(X_1, X_2, X_3 \ldots, P_1, P_2, P_3 \ldots)$, Brookfield Viscosity=$f_6(X_1, X_2, X_3 \ldots, P_1, P_2, P_3 \ldots)$, Soot-dispersancy=$f_7(X_1, X_2, X_3 \ldots, P_1, P_2, P_3 \ldots)$, Oxidation=$f_8(X_1, X_2, X_3 \ldots, P_1, P_2, P_3 \ldots)$, Deposit=$f_9(X_1, X_2, X_3 \ldots, P_1, P_2, P_3 \ldots)$, Wear=$f_{10}(X_1, X_2, X_3 \ldots, P_1, P_2, P_3 \ldots)$, Sulfur=$f_{11}(X_1, X_2, X_3 \ldots, P_1, P_2, P_3 \ldots)$, Phosphorus=$f_{12}(X_1, X_2, X_3 \ldots, P_1, P_2, P_3 \ldots)$, Base Number (BN)=$f_{13}(X_1, X_2, X_3 \ldots, P_1, P_2, P_3 \ldots)$, Color=$f_{14}(X_1, X_2, X_3 \ldots, P_1, P_2, P_3 \ldots)$, Ash Content=$f_{15}(X_1, X_2, X_3 \ldots, P_1, P_2, P_3 \ldots)$, Aniline Point=$f_{16}(X_1, X_2, X_3 \ldots, P_1, P_2, P_3 \ldots)$, Acid Number (AN)=$f_{17}(X_1, X_2, X_3 \ldots, P_1, P_2, P_3 \ldots)$, Viscosity Index=$f_{18}(X_1, X_2, X_3 \ldots, P_1, P_2, P_3 \ldots)$, Turbidity=$f_{19}(X_1, X_2, X_3 \ldots, P_1, P_2, P_3 \ldots)$, Demulsibility=$f_{20}(X_1, X_2, X_3 \ldots, P_1, P_2, P_3 \ldots)$, Foam Stability=$f_{21}(X_1, X_2, X_3 \ldots, P_1, P_2, P_3 \ldots)$, Acute Toxicity=$f_{22}(X_1, X_2, X_3 \ldots, P_1, P_2, P_3 \ldots)$, Biodegradability=$f_{23}(X_1, X_2, X_3 \ldots, P_1, P_2, P_3 \ldots)$, Nitrogen=$f_{24}(X_1, X_2, X_3 \ldots, P_1, P_2, P_3 \ldots)$, Detergency=$f_{25}(X_1, X_2, X_3 \ldots, P_1, P_2, P_3 \ldots)$, where $X_1$, $X_2$, $X_3$ . . . are the wt %, vol %, or the mole fractions of components 1, 2, 3 . . . and $P_1$, $P_2$, $P_3$ . . . area subset of the properties of the corresponding components, KV=kinematic viscosities, CCS=cold cranking simulator, HTHS=high temperature, high shear viscosity, MRV=mini-rotary viscometer, (b) determining the characteristic of the lubricant, adjusting the base stocks and additives based on measurements of the characteristics of the lubricant, continuing to iteratively adjust the amount of the base stocks and additives until the lubricant meets the predetermined characteristics based on costs and properties of base stocks and additives, wherein blend adjustments and corrections to the lubricant are made using functions based on on-line sensors in raw materials and finished product tanks.

2. The method of claim 1 wherein the function is determined using lab-scale high throughput blending and testing.

3. The method of claim 1 wherein blend adjustments and corrections are made dynamically using an integrated feedback loop.

4. The method of claim 1 wherein said functions result in reduction of variations in finished lubricant characteristics between 30 and 90%.

5. The method of claim 1 wherein said functions result in reduction of variations in finished lubricant characteristics between 50 and 90%.

6. The method of claim 1 wherein said functions result in reduction of variations in finished lubricant characteristics between 75-90%.

7. The method of claim 1 further comprising the step of making measurements on the blended lubricant and adjusting the combination of base stocks and additives.

8. A method to optimize the blending of base stocks and additives to form a finished lubricant having predetermined characteristics comprising:

a) obtaining a model that relates the characteristics of a lubricant to a combination of the amount and properties of the base stocks and additives, wherein said predetermined characteristics include more than one of the following: $KV=f_1(X_1, X_2, X_3 \ldots, P_1, P_2, P_3 \ldots)$, $CCS=f_2(X_1, X_2, X_3 \ldots, P_1, P_2, P_3 \ldots)$, $HTHS=f_3(X_1, X_2, X_3 \ldots, P_1, P_2, P_3 \ldots)$, Noack Volatility=$f_4(X_1, X_2, X_3 \ldots, P_1, P_2, P_3 \ldots)$, $MRV=f_5(X_1, X_2, X_3 \ldots, P_1, P_2, P_3 \ldots)$, Brookfield Viscosity=$f_6(X_1, X_2, X_3 \ldots, P_1, P_2, P_3 \ldots)$, Soot-dispersancy=$f_7(X_1, X_2, X_3 \ldots, P_1, P_2, P_3 \ldots)$, Oxidation=$f_8(X_1, X_2, X_3 \ldots, P_1, P_2, P_3 \ldots)$, Deposit=$f_9(X_1, X_2, X_3 \ldots, P_1, P_2, P_3 \ldots)$, Wear=$f_{10}(X_1, X_2, X_3 \ldots, P_1, P_2, P_3 \ldots)$, Sulfur=$f_{11}(X_1, X_2, X_3 \ldots, P_1, P_2, P_3 \ldots)$, Phosphorus=$f_{12}(X_1, X_2, X_3 \ldots, P_1, P_2, P_3 \ldots)$, Base Number (BN)=$f_{13}(X_1, X_2, X_3 \ldots, P_1, P_2, P_3 \ldots)$, Color=$f_{14}(X_1, X_2, X_3 \ldots, P_1, P_2, P_3 \ldots)$, Ash Content=$f_{15}(X_1, X_2, X_3 \ldots, P_1, P_2, P_3 \ldots)$, Aniline Point=$f_{16}(X_1, X_2, X_3 \ldots, P_1, P_2, P_3 \ldots)$, Acid Number (AN)=$f_{17}(X_1, X_2, X_3 \ldots, P_1, P_2, P_3 \ldots)$, Viscosity Index=$f_{18}(X_1, X_2, X_3 \ldots, P_1, P_2, P_3 \ldots)$, Turbidity=$f_{19}(X_1, X_2, X_3 \ldots, P_1, P_2, P_3 \ldots)$, Demulsibility=$f_{20}(X_1, X_2, X_3 \ldots, P_1, P_2, P_3 \ldots)$, Foam Stability=$f_{21}(X_1, X_2, X_3 \ldots, P_1, P_2, P_3 \ldots)$, Acute Toxicity=$f_{22}(X_1, X_2, X_3 \ldots, P_1, P_2, P_3 \ldots)$, Biodegradability=$f_{23}(X_1, X_2, X_3 \ldots, P_1, P_2, P_3 \ldots)$, Nitrogen=$f_{24}(X_1, X_2, X_3 \ldots, P_1, P_2, P_3 \ldots)$, Detergency=$f_{25}(X_1, X_2, X_3 \ldots, P_1, P_2, P_3 \ldots)$, where $X_1, X_2, X_3 \ldots$ are the wt %, vol %, or the mole fractions of components 1, 2, 3 ... and $P_1, P_2, P_3 \ldots$ area subset of the properties of the corresponding components, KV=kinematic viscosities, CCS=cold cranking simulator, HTHS=high temperature, high shear viscosity, MRV=mini-rotary viscometer, b) determining the combination of base stocks and additives to form the lubricant having the predetermined characteristics from a series of models, c) measuring the characteristics of the lubricant from step b), and d) adjusting the blend by optimizing the combination of base stocks and additives to meet the predetermined characteristics based on base stocks and additives costs and availability wherein blend adjustments and corrections to the lubricant are made using functions based on on-line sensors in raw materials and finished product tanks.

9. The method of claim 8 wherein said predetermined characteristic include KV (kinematic viscosities), CCS (cold cranking simulator), HTHS (high temperature, high shear viscosity), Noack Volatility, MRV (mini-rotary viscometer), Brookfield V, Soot-Dispersancy, Oxidation, Deposit, Wear, Sulfur, Phosphorus, Base Number, Color, Ash Content, Aniline Point, Acid Number, Viscosity Index, Turbidity, Demulsibility, Foam Stability, Acute Toxicity, Biodegradability, Nitrogen, and Detergency.

10. The method of claim 9 wherein said predetermined characteristics are described as $KV=f_1(X_1, X_2, X_3 \ldots, P_1, P_2, P_3 \ldots)$, $CCS=f_2(X_1, X_2, X_3 \ldots, P_1, P_2, P_3 \ldots)$, $HTHS=f_3(X_1, X_2, X_3 \ldots, P_1, P_2, P_3 \ldots)$, Noack Volatility=$f_4(X_1, X_2, X_3 \ldots, P_3, P_2, P_3 \ldots)$, Oxidation=$f_5(X_1, X_2, X_3 \ldots, P_1, P_2, P_3 \ldots)$, Deposit=$f_6(X_1, X_2, X_3, \ldots, P_1, P_2, P_3 \ldots)$, Wear=$f_7(X_1, X_2, X_3 \ldots, P_1, P_2, P_3 \ldots)$, Sulfur=$f_8(X_1, X_2, X_3 \ldots, P_1, P_2, P_3 \ldots)$, Phosphorus=$f_9(X_1, X_2, X_3 \ldots, P_1, P_2, P_3 \ldots)$, Base Number (BN)=$f_{10}(X_1, X_2, X_3 \ldots, P_1, P_2, P_3 \ldots)$, Color $f_{11}(X_1, X_2, X_3 \ldots, P_1, P_2, P_3 \ldots)$, Ash Content=$f_{12}(X_1, X_2, X_3, \ldots, P_1, P_2, P_3 \ldots)$, Aniline Point=$f_{13}(X_1, X_2, X_3 \ldots, P_1, P_2, P_3 \ldots)$, Acid Number (TAN)=$f_{14}(X_1, X_2, X_3 \ldots, P_1, F_2, P_3 \ldots)$, Viscosity Index=$f_{15}(X_1, X_2, X_3 \ldots, P_1, P_2, P_3 \ldots)$, Turbidity=$f_{15}(X_1, X_2, X_3 \ldots, P_1, P_2, P_3 \ldots)$, Demulsibility=$f_{16}(X_1, X_2, X_3 \ldots, P_1, P_2, P_3 \ldots)$, Foam Stability=$f_{17}(X_1, X_2, X_3 \ldots, P_1, P_2, P_3 \ldots)$, Acute Toxicity=$f_{18}(X_1, X_2, X_3 \ldots, P_1, P_2, P_3 \ldots)$, Biodegradability=$f_{19}(X_1, X_2, X_3 \ldots, P_1, P_2, P_3 \ldots)$, Nitrogen=$f_{24}(X_1, X_2, X_3 \ldots, P_1, P_2, P_3, \ldots)$, Detergency=$f_{25}(X_1, X_2, X_3, \ldots, P_1, P_2, P_3 \ldots)$, where $X_1, X_2, X_3 \ldots$ are the wt %, vol %, or the mole fractions of components 1, 2, 3 ..., and $P_1, P_2, P_3 \ldots$ are a subset of the properties of the corresponding components.

* * * * *